(12) United States Patent
Genet (10) Patent No.: US 6,277,091 B1
(45) Date of Patent: Aug. 21, 2001

(54) ASSEMBLY FOR THE DISTRIBUTION OF A PHARMACEUTICAL SOLUTION IN A MULTI-DOSE VIAL INTO SINGLE-DOSE CAPSULES FOR SINGLE USE

(75) Inventor: Alain Genet, Ecully (FR)

(73) Assignee: Pasteur Merieux Serums & Vaccins, Lyons (FR)

( * ) Notice: Subject to any disclaimer, the term of this patent is extended or adjusted under 35 U.S.C. 154(b) by 0 days.

(21) Appl. No.: 08/702,539

(22) PCT Filed: Mar. 1, 1995

(86) PCT No.: PCT/FR95/00240

§ 371 Date: Nov. 4, 1996

§ 102(e) Date: Nov. 4, 1996

(87) PCT Pub. No.: WO95/23576

PCT Pub. Date: Sep. 8, 1995

(30) Foreign Application Priority Data

Mar. 4, 1994 (FR) ................................................. 94 02526

(51) Int. Cl.[7] ............................................................... A61J 1/20
(52) U.S. Cl. ............................ 604/82; 604/89; 604/232; 604/68

(58) Field of Search .............................. 424/45; 604/232, 604/68, 82, 89, 187, 195, 218, 239, 240; 92/21 R (56) References Cited

U.S. PATENT DOCUMENTS

| 3,672,369 | 6/1972 | Brown | 128/261 |
|---|---|---|---|
| 4,125,186 | * 11/1978 | Meierhoefer | 206/221 |
| 4,342,395 | * 8/1982 | Brown | 206/530 |
| 4,581,015 | * 4/1986 | Alfano | 604/88 |
| 4,842,028 | 6/1989 | Kaufman et al. | 141/114 |

FOREIGN PATENT DOCUMENTS

| 0 327 519 | 1/1989 | (EP) . |
|---|---|---|
| 92/15347 | 9/1992 | (WO) . |

* cited by examiner

*Primary Examiner*—Raj Bawa
(74) *Attorney, Agent, or Firm*—Larson & Taylor PLC (57) ABSTRACT

Assembly for the distribution of a pharmaceutical solution, contained in multi-dose vial, into single-dose carpules for single use, comprising single-dose carpules and a distribution apparatus, in which assembly pressure and suction means are provided to circulate a liquid from the carpules to the vial and from the vial to the carpules, by means of a network of channels.

10 Claims, 7 Drawing Sheets

FIG. 14

ASSEMBLY FOR THE DISTRIBUTION OF A PHARMACEUTICAL SOLUTION IN A MULTI-DOSE VIAL INTO SINGLE-DOSE CAPSULES FOR SINGLE USE

This application is a 371 of PCT/FR95/00240, filed Mar. 1, 1995.

BACKGROUND OF THE INVENTION

The present invention relates to an assembly for the distribution of a pharmaceutical solution, contained in multi-dose vial, into single-dose carpules for single use, or the like, and more particularly for dissolving a lyophilized pharmaceutical product contained in such a vial and distributing the pharmaceutical solution obtained. The invention is particularly advantageously applicable in the case of vaccines which are intended to be stored in lyophilized form until they are used and which therefore require separate presentation of the lyophilized active principle and the solvent. It is preferably applicable to pressurized-jet injection (needleless injection).

The invention also relates to sets of single-dose carpules in the form of clusters, to improved plungers for carpules, to an apparatus especially designed for dissolving lyophilized vaccines and for distribution into carpules, as well as to a process for doing this.

For parenteral administration of medicinal substances, and in particular for vaccination, use is being increasingly made of needleless injection apparatuses which deliver the dose in the form of a very thin and very powerful jet. These applications have been developed not only in veterinary medicine but also in human medicine, since the absence of an injection needle makes it possible to use personnel trained in a short time, to speed up the administration procedure and to avoid the bacterial and, above all, viral infections which may occur if the same injection nozzle is used without sterilization between two or more subjects, which is current practice.

The most advanced transcutaneous jet injection apparatuses use single-use carpules equipped with their own nozzle, which nozzle is intended to be the only part in contact with the skin of the patient during the injection, eliminating the risk of cross-infection, given that the carpule and therefore the nozzle is changed on each injection.

However, it has to date only been possible to use this type of apparatus for ready-to-use vaccines, prepackaged in individual doses in single-dose (one-dose) carpules. Such carpules are, for example, known under the brand name Imule.

The problem remains the same in the case of pharmaceutical products which are preserved only in a lyophilized form and which must therefore be redissolved at the time of use. This is particularly true in the case of vaccines, many of which must be preserved in the lyophilized form.

Packaging them therefore makes it necessary to provide a vial of solvent and a vial of lyophilized active product. Use is then made of a large syringe with which the solvent is recovered, and this solvent is then injected into the vial of lyophilized product. Next, after agitation, the pharmaceutical solution ready for use can be taken up with the aid of a number of single-use syringes equal to the number of doses contained in the vial of lyophilized product.

However, it will be recalled that, in practice, further to the risks of cross-infection when the same needle is used without sterilization for treating several subjects, there is also a high risk of contamination during the operations of redissolving the lyophilized products.

Other major drawbacks are the inaccuracy of the doses administered and the fact that it is difficult to make up the intended number of doses from a given vial of vaccine. This is because, even for experienced individuals, it cannot be guaranteed that the intended number of doses will be administered unless an excess of vaccine is provided, which then leads to a higher cost. Note will, in particular, be made of the loss of product during the operation consisting in purging the air contained in the syringe before administration.

The object of the present invention is thus to provide an assembly which makes it possible, in particular, to dissolve lyophilized pharmaceutical products and distribute them into single-dose carpules for single use, or the like, under optimum conditions of safety, in particular sterility, and efficiency, while making it possible to use conventional vials of lyophilized pharmaceutical products.

Another object of the invention is to provide such an assembly which is compact, which is easy to use in complete safety and which is inexpensive and reliable, so as to permit large-scale use under optimal conditions, in particular in countries in which mass treatments or vaccinations need to be carried out.

Yet another object is to provide such an assembly which can at the same time be used simply for distributing a ready-to-use solution into such carpules.

BRIEF SUMMARY OF THE INVENTION

The subject of the present invention is an assembly for the distribution of a pharmaceutical solution, contained in multi-dose vial, into single-dose carpules for single use, or similar devices, in particular for dissolving a lyophilized pharmaceutical product contained in such a vial and distributing the pharmaceutical solution obtained, comprising single-dose carpules for single use and a distribution apparatus in which assembly pressure/suction means are provided, which are designed to make it possible to circulate a liquid from the carpules to the vial and from the vial to the carpules, by means of a network of suitable channels, and optionally a vial of liquid or lyophilized pharmaceutical product.

Means are preferably provided for controlling the volume of pharmaceutical solution introduced into the carpules. Control should be taken to mean uniform distribution into the carpules while preventing any air from entering them, and advantageously also controlling the quantity of solution introduced into the carpules. In fact, in the case of lyophilized products, it is preferable for the solvent to be contained in the carpules and, in order to compensate for losses of solvent due to the dead volume and to prevent any air from entering the carpules, it is preferable for them to initially contain a volume slightly greater than the take-up volume. In other words, after take-up, a volume slightly less than the initial volume is introduced into the carpules.

Preferably, the single-dose carpules are formed by a cylindrical body which defines an internal volume in which a plunger slides in leaktight fashion, this plunger being designed to vary the internal volume, the plungers of the single-dose carpules being used as suction/pressure means for circulating the liquid from the carpules to the vial and vice versa. Preferably, the cylindrical body of the single-dose carpules is closed at one end by a neck having a central orifice forming a nozzle for pressurized-jet injection, the plunger being also designed to transmit to the liquid the pressure of an injector and hence form this jet.

DETAILED DESCRIPTION OF THE INVENTION

In the preferred embodiment of the invention, the carpules are presented in groups of more than one and are mounted in leaktight fashion and removably on a support piece which has internally a central channel which supplies each of the single-dose carpules of the group via collateral channels, the central channel opening into an end of the support piece which is designed so that the central channel can be connected to the internal volume of a multi-dose vial. This presentation makes it possible to work with great ease and quickly.

Preferably, the distribution apparatus includes a housing into which the single-dose carpules (optionally the support piece combining the carpules) are removably fitted, thrust rods, each arranged so that they can engage removably with the plunger of a carpule and actuation means for displacing the thrust rods, and thereby the plungers of the carpules, in the direction tending to reduce the internal volume of these carpules, or in the opposite direction, means being furthermore provided in order, in the latter case, to release the engagement between the plungers and the thrust rods, and at the same time to control the volume introduced into each carpule, so that each carpule then contains the required volume of pharmaceutical solution. This simple and reliable arrangement is highly advantageous, since it makes it possible to suck the solution into the carpules simultaneously and at the same rate and, when the required volume has been taken in, to release the carpules which are then ready for use. It highly advantageously also makes it possible to prevent any air from being introduced into the carpules.

The means for releasing the engagement between the plunger and the thrust rods may advantageously be calibrated annular pieces which are located on the apparatus and the external diameter of which is slightly smaller than the internal diameter of the body of the carpule, the annular pieces being designed to be located inside a carpule body so as to form a stop for the plunger when it is displaced in the direction tending to increase the internal volume of the carpule.

The combination of the engagement means between the thrust rods and the plunger and of the means of the annular piece type allows the expected functions to be ensured perfectly, and in a remarkably simple and reliable fashion, without reporting to complex mechanical, hydraulic and/or control means. The precise effect of this simplicity is that it is possible to resort to the advantageous clusters of carpules of the invention, The support piece may present carpules on one face or on two opposite faces. Presentation on a single face is preferred.

Preferably, each thrust rod is equipped at one end with an engagement means which is complementary to an engagement means located on the plungers of the carpules.

The assembly according to the invention may incorporate the clusters of carpules and/or support pieces and/or distribution apparatuses as described above.

A further subject of the invention is a cluster of single-dose carpules for single use which are intended for pressurized-jet injection of a pharmaceutical solution and are combined on a support piece. The support piece preferably internally includes a network of channels which are designed so as to supply the carpules. Preferably, the carpules may comprise an end which has a thin orifice and forms an injection nozzle, whereas the support piece can comprise receptacles in which the carpule ends forming the injection nozzle are placed in leaktight fashion and removably, and whereas the network of channels of the support piece in each case can comprise a collateral channel opening into the receptacle opposite the thin orifice of the injection nozzle of the fitted carpule.

In a preferred embodiment of the invention, the support piece includes the carpules on a single face. Then, preferably, the elongate support piece may include a central channel into which a spindle which can move in rotation in this channel is inserted, this spindle being provided with a groove extending along the spindle and over a part of its length, the groove being designed so that it can connect the carpules or interrupt this connection, and with a slot, whereas the support piece includes an outlet orifice which opens into the central channel in front of the slot. The carpules are preferably arranged in a row.

This embodiment has the advantage of isolating each carpule individually by eliminating any connection between the carpules. This makes it possible to use the carpules in stages over time without risk of contamination.

In order to ensure suitable leaktightness, it is preferred to use a support piece made of flexible material, for example rubber or any other elastic material accepted by the pharmacopoeia. A reinforcement may then be added to it in order to stiffen it.

In a second embodiment, the support piece may also have an elongate shape with two rows of carpules arranged in the same plane, on either side of the support piece. Of course, it may have any other suitable shape and even have more than two rows of carpules, or alternatively have only one such row.

Preferably, in this second embodiment, the support piece internally includes a central channel which opens into one end and from which the collateral channels extend. The support piece may advantageously be formed integrally of moulded plastic, which makes it possible to obtain highly favourable production costs which are compatible with the single usage for which this piece is intended.

The support pieces according to the invention may be designed so that they can be connected to a conventional needle intended to penetrate the stopper of the vial of lyophilized pharmaceutical product in order to introduce the solvent into it, then withdraw it after reconstitution of the pharmaceutical solution, in the case of lyophilized products.

Preferably, the carpules comprise a cylindrical body which defines an internal volume, and a plunger designed to move in leaktight fashion in the said body in order to vary the internal volume which, when the plunger is in its extreme retracted position, is greater by a controlled value than the dose volume for which the carpule is intended, which makes it possible to compensate for the unavoidable losses of solvent on the walls of the vial of lyophilized pharmaceutical product and in the needle and the channels of the support piece (dead volume), and to prevent any air from entering the carpules.

The carpules may highly advantageously comprise a plunger having an external face provided at its centre with a recess which widens towards the middle of the plunger.

A further subject of the invention is a support piece used for joining single-dose carpules for single use or the like, and for making liquid flow from and to these carpules, comprising an elongate body provided with a central channel and with collateral channels opening outside and in this channel, which central channel has a spindle which can move in rotation in this channel inserted into it, this spindle including a groove extending along the spindle and over a part of its length and being designed so that it can be brought in front of the collateral channels in order to connect them, and a slot, whereas the support piece includes an outlet orifice which opens into the central channel in front of the groove. Preferably, the elongate body is made of flexible material, rubber or other elastic material accepted by the pharmacopoeia, and may be combined with a rigid reinforcement. Also preferably, the elongate body includes receptacles, into which the collateral channels open and which are fitted to the carpules.

A further subject of the invention is a plunger for a carpule intended for pressurized injection of a pharmaceutical solution, which is especially designed for the carpules according to the invention and for the use which is made thereof and which is described above. These plungers are characterized in that they include, on their face which is external with respect to the rest of the carpule, a positive engagement means which may advantageously comprise a central recess which widens towards the middle of the plunger.

A further subject of the invention is carpules, for pressurized-jet injection, which are fitted with such a plunger.

A further subject of the invention is an apparatus for the distribution of a pharmaceutical solution, contained in multi-dose vial, into single-dose carpules for single use, or the like, in particular for dissolving a lyophilized pharmaceutical product and distributing the pharmaceutical solution obtained, comprising a housing bounded on at least one side by a structure which is fixed or can move in the plane of the housing, and by thrust rods, or similar means, which pass through the structure via suitable equidistant holes and can move in the plane of the housing by sliding in the holes.

Preferably, at its end located next to the housing, each thrust rod includes a positive engagement means, which may advantageously comprise a stud equipped with a terminal head connected to the thrust rod by a part of smaller cross-section.

It is preferable to associate a calibrated annular lip, which projects into the housing, with each hole of the structure.

The thrust rods may be supported by external jaws which can move in the plane of the housing. Also preferably, if the mobile structures or internal jaws can be normally pressed towards one another by return springs, the external jaws will be displaceable in translation in both directions by an actuation means which may be manual or motorized. Preferably, each external jaw is equipped with a stop means which keeps the associated internal jaw open, against the action of its return spring.

The apparatus may be designed for a cluster of carpules in which the carpules are arranged on a single side of the support piece, which is the preferred case, or on two sides. In the latter case, two sets of jaws which can be moved in translation in the plane of the housing of the carpules are provided: an internal set of jaws defining the housing and having equidistant holes, and an external set of jaws supporting the thrust rods, which are guided in translation in the said holes, and the annular pieces being annular lips located on the internal jaws and bordering the aperture of the holes on the housing side.

Finally, the apparatus according to the invention may include a support for holding a multi-dose vial, it being advantageously possible for this support to be an adjustable support intended to hold different sizes of vial.

A further subject of the invention is a process for dissolving a lyophilized pharmaceutical product contained in a multi-dose vial and for distributing it into single-dose carpules for single use or the like, in particular for pressurized-jet injection, in which use is made of single-dose carpules containing the solvent intended for the lyophilized product, the solvent contained in the carpules is passed into the vial of lyophilized product, agitation is carried out so as to dissolve the product fully, then the pharmaceutical solution thus produced is distributed in doses into the single-dose carpules.

Preferably, single-dose carpules containing an excess of solvent are selected at the start in order to compensate for losses of solvent during the process.

BRIEF DESCRIPTION OF THE DRAWINGS

The invention will now be described in more detail with the aid of two illustrative embodiments of clusters of carpules and of apparatuses according to the invention, in conjunction with the appended drawing, in which.

The carpule 1 according to the invention is made of polypropylene. It includes a cylindrical body 2 which is open at its rear end 3 and is closed at its front end 4 by an end wall 5 which continues in a constricted part or neck 6 which contains the finely calibrated injection nozzle 7 opening into the internal volume 8 of the body 2. 0.60 ml of solvent for the lyophilized vaccine is contained in the volume 8 which is closed at its rear end by a plunger 9, forming a perfect seal and made integrally of elastomer.

Figure 2:
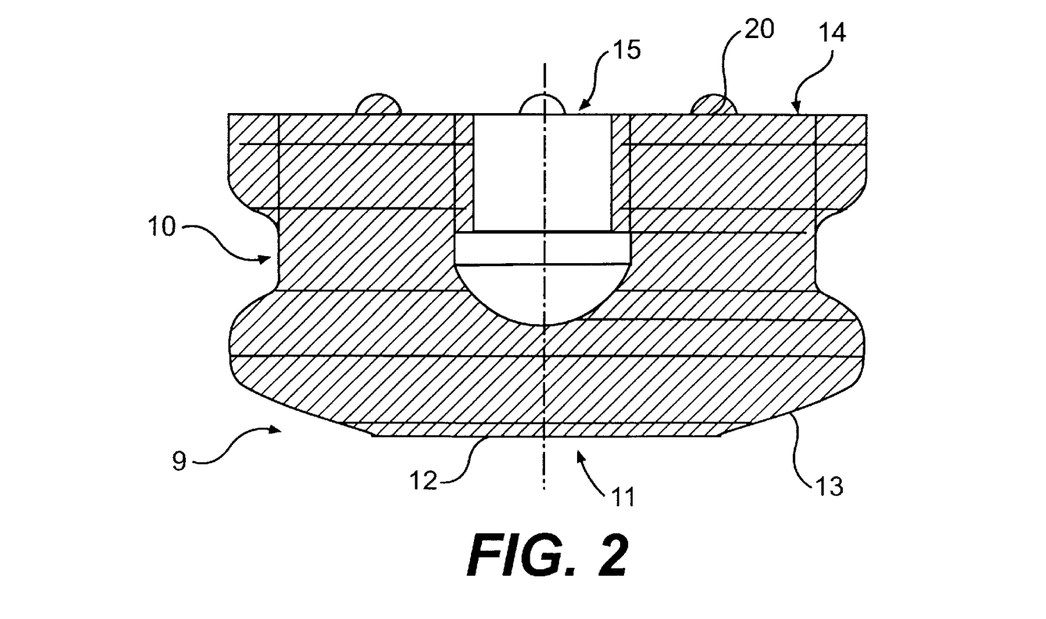
FIG. 2 represents a view in median section of a carpule plunger according to the invention.

The plunger 9 is represented in detail and on large scale in FIG. 2, which shows its essentially cylindrical shape, having a circumferential recess 10 whose edges are inclined by approximately 30° with respect to a plane transverse to the generatrix of the cylinder. The leading face 11 of the plunger 9 has a central part 12 which coincides with the base of the cylinder, and a slightly inclined peripheral part 13. This shape allows this face of the plunger to fit the end wall 5 when the plunger has been actuated.

The opposite face of the plunger 9, which is the face located externally with respect to the volume 8, and is denoted by the reference 14, is essentially plane but has a central recess 15 which extends, centred on the axis, in a first cylindrical part 16, a second cylindrical part 17, of slightly greater diameter, thus forming a shoulder 18, then in a part in the form of a spherical cap 19 whose base has the same diameter as the part 17. The face 14 furthermore has four spikes 20 which are equidistant from each other and also with respect to the axis of the cylinder and are involved in the manufacture of the plungers, in particular for releasing them from the mould.

Referring again to FIG. 1, this figure shows a cluster 21 of ten identical carpules 1, of the Imule® type, each fixed removably but in leaktight fashion by its neck 6 into a suitable receptacle 22 supported by the piece referenced 23. To this end, this elongate piece has a series of five receptacles 22 on its two opposite faces 24 and 25, and a thin central channel 26 supplying each of the receptacles 22 at their centre, via collateral channels 27 opening in front of the injection nozzles 7. The central channel 26 opens at one end 28 of the piece 23, which end 28 is designed so that a needle 29 of conventional type can be fitted onto it. The piece 23 is made of plastic and is obtained, with its central channel and its collateral channels, integrally by moulding. When they are suitably mounted on the piece 23, the carpules 1 are edge to edge.

Figure 5:
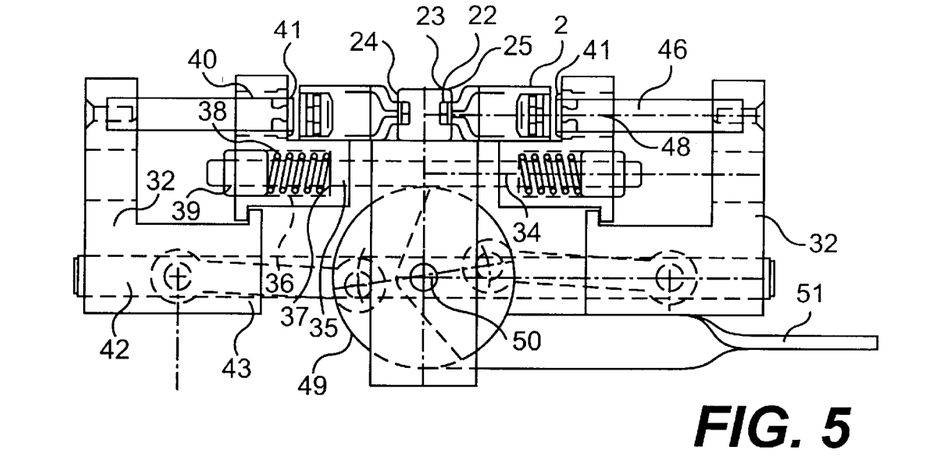
FIGS. 5 to 7 are partial views in cross-section, intended to show the mode of operation of the apparatus in FIGS. 3 and 4.
Figure 6:
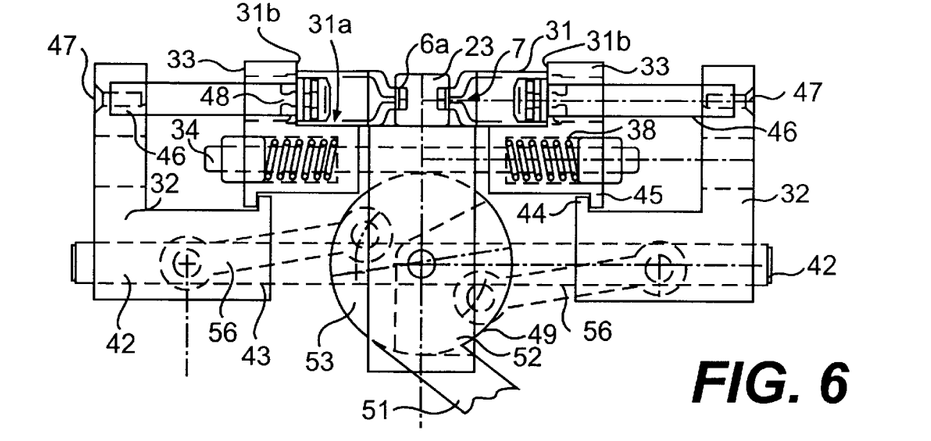
Figure 7:
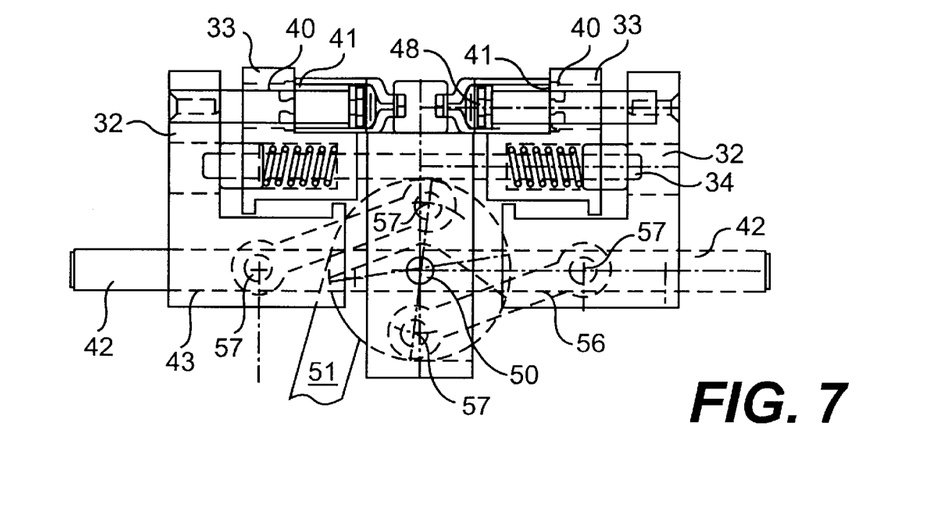

It will be noted that FIGS. 5 to 7 show carpules 1 whose neck 6 additionally has a small lip 6a which is intended, if necessary, to improve the retention of the carpules 1 to the piece 23.

For its preferred application to lyophilized vaccines, the cluster 21 is sterilely packaged with its ten carpules 1 filled with the suitable solvent (0.6 ml per carpule for carpules intended to contain 0.5 ml of vaccine in solution).

Reference will now be made to FIGS. 3 to 7, which relate to an apparatus 30 intended to hold the cluster 21 of carpules and the vial 31 of lyophilized vaccine, in order to carry out all the operations of preparing the ready-to-use vaccine and distributing it accurately into the carpules.

The apparatus 30 firstly comprises a housing 31 for holding a cluster 21 of carpules so that they are centred. It also comprises two sets jaws: external jaws 32 and internal jaws 33, the latter having a general L-shape and being positioned opposite one another so as to define the housing 31, as can more particularly be seen in FIGS. 5 to 7, the base of the L forming the end wall 31a of the housing, and the branches of the L forming the edges 31b. The internal jaws 33 are mounted so that they can move in translation on two spindles 34 which are parallel to the plane of the housing 31 and therefore to the plane of the cluster 21 of carpules when it is fitted.

These spindles 34 extend in holes 35 made in the internal jaws 33, in the base of the L which forms the end wall of the housing 31, these holes 35 having a part 36 with larger dimensions (in width or in diameter), which provides shoulders 37. Coil return springs 38 extend concentrically with the spindles 34 in the part 36 of the holes 35, between the ends of the spindles 34, where they are held by bolts 39, and the shoulders 37. These springs 38 therefore push each of the internal jaws 33 towards one another, that is to say in the direction of the cluster 21 mounted in the housing 31. The bolts 39 may allow the application pressure of the springs 38 to be adjusted. A safety lock means may be combined with them.

The branches of the L which form the edges 31b of the housing 31 each have five equidistant holes 40, designed so as to be placed exactly facing the rear end 3 of a carpule 1 of the fitted cluster 21. The diameter of the holes 40 is less than that of the plungers 9 of the carpules 1. A small annular lip 41, which projects inside the housing 31, is associated with each hole 40. The internal diameter of this lip 41 is identical to the internal diameter of the holes 40, whereas its external diameter is substantially identical to that of the plunger 9 of the carpules 1, which means that it is suitable for being inserted into the carpule 1 via the rear end thereof when the plunger 9 is pushed.

The external jaws 32 of the apparatus 30 also have an L-shape and are mounted so as to slide on two parallel spindles 42 contained in a plane parallel to the plane of the spindles 34 of the internal jaws 33.

The spindles 42 pass through the bases of the L via holes 43, and the jaws 32 are prevented from being released by virtue of shoulders 44 which bear against corresponding shoulders 45 on the internal jaws 33. Five equidistant thrust rods 46 are fixed to each branch of the L. A part of each thrust rod penetrates the body of the branch of the L, in a suitable hole, to be fixed therein using a screw 47. The thrust rods 46 then extend through holes 40 which are made in the internal jaws 33 and in which they can slide. At their free end, the thrust rods 46 have a stud 48 having a shape complementary to the central recess 15 of the plungers 9, which means that these studs 48 can engage removably with these recesses.

As can be seen in FIGS. 5 to 7, the annular lip 41 of the internal jaw 33 may form part of a single piece which at the same time forms the sleeve in which the associated thrust rod 46 slides and which is placed in a suitable hole 40.

Figure 3:
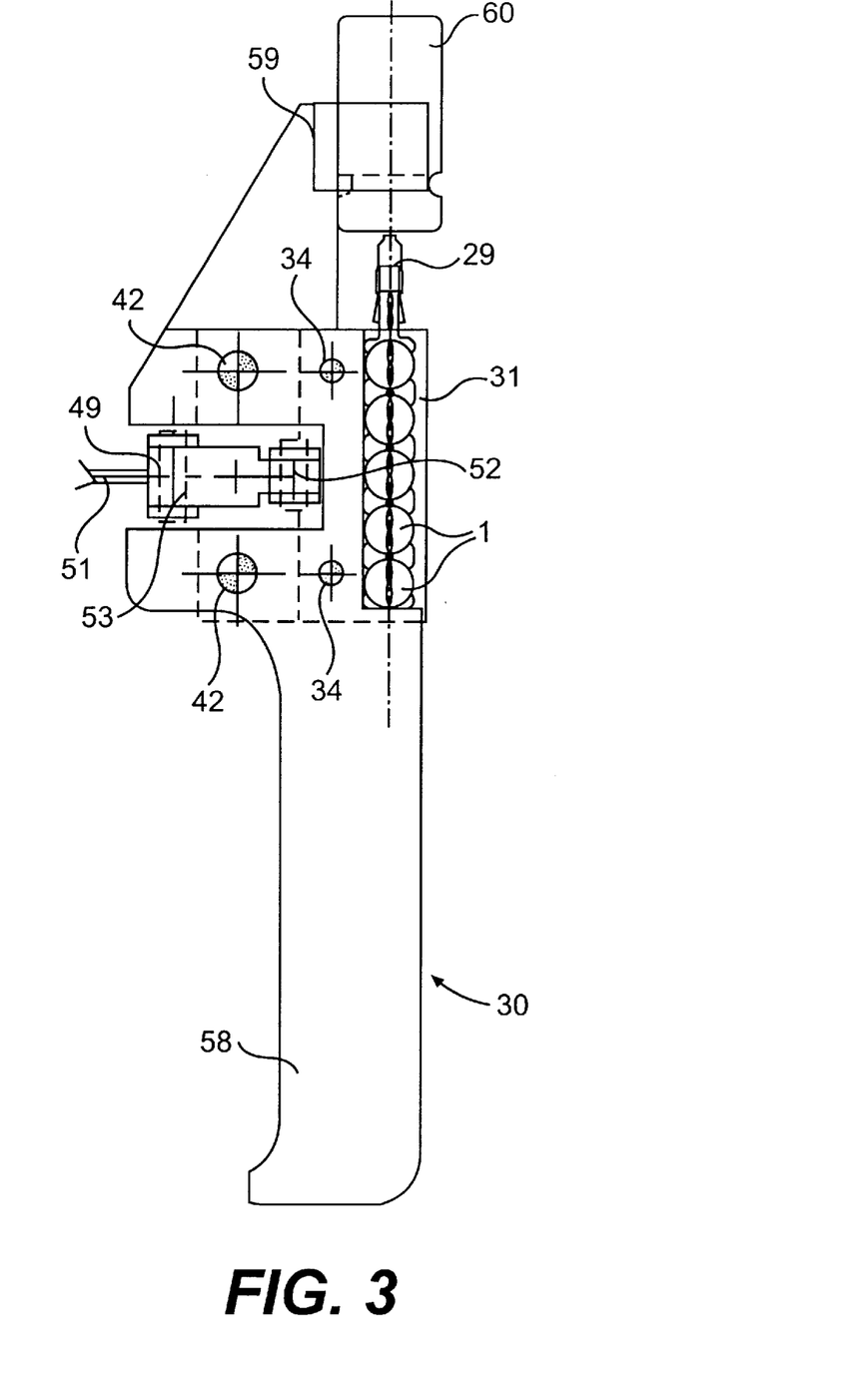
FIG. 3 represents a side view of an apparatus according to the invention, on which the assembly in FIG. 1 is mounted, the apparatus being represented without the internal and external jaws.
Figure 4:
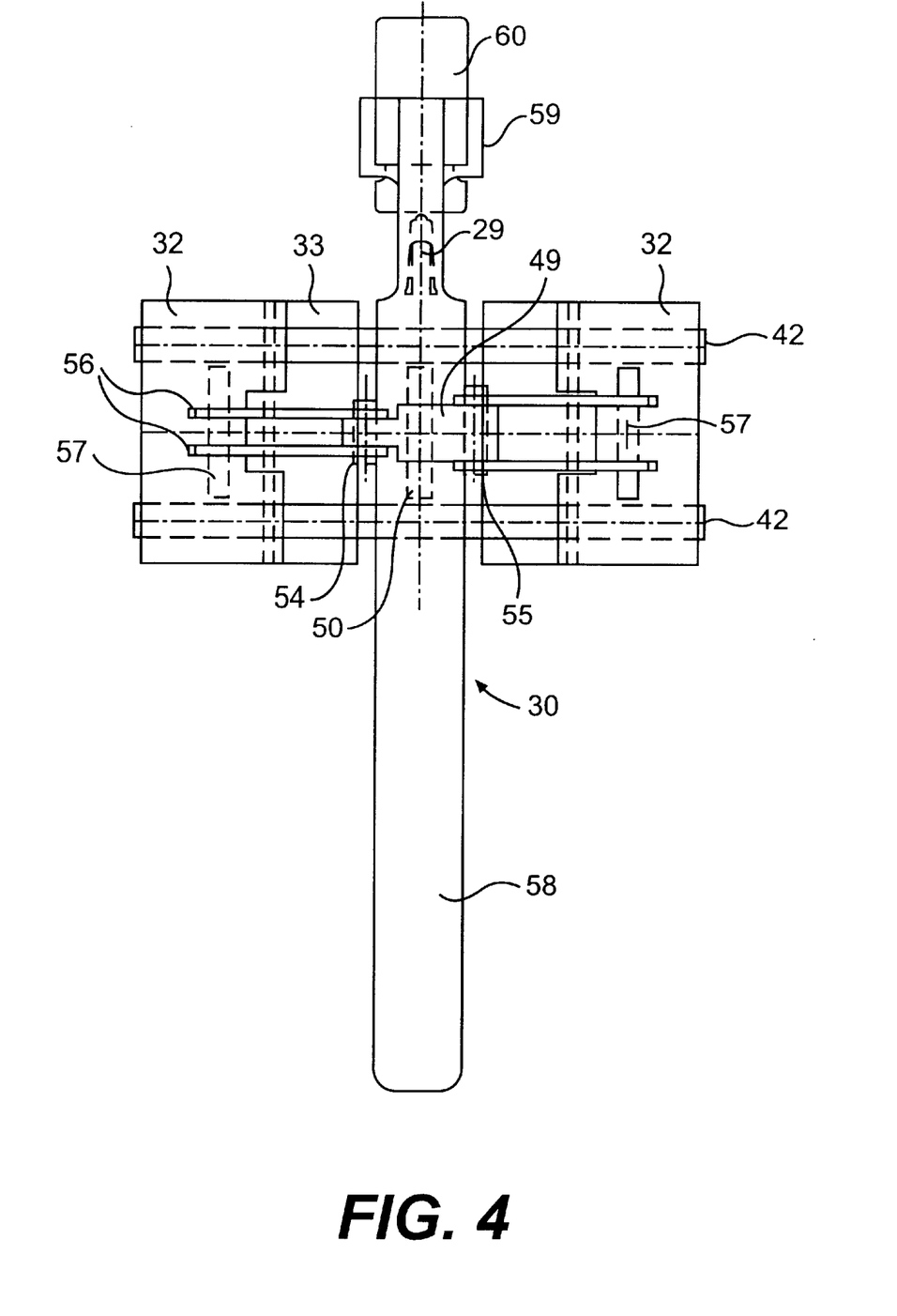
FIG. 4 is a plan view of the representation in FIG. 3, the apparatus being here represented with its jaws.

The external jaws 32 are actuated in the direction tending to move them in translation with respect to the spindles 42, by an actuation device comprising a crank plate 49 journaled on the apparatus 30 on a spindle 50, the profile of which crank plate is seen in FIGS. 3 and 4, and the plan shape of which crank plate is seen in FIGS. 5 to 7. A operating lever 51 is secured to the crank plate 49 and is used for actuating it. The crank plate 49 is in the form of a disc having a part 52 of small thickness and a thicker part 53. Each of these parts 52 and 53 has a hole, 54 and 55 respectively, the axes of these holes and the spindle 50 being aligned, and the holes being each located at a same distance from the spindle 50.

As clearly shown in FIG. 4, two double link rods 56 are journaled with respect to the holes 54 and 55 and, at their other ends, onto the external jaws 32 by means of spindles 57 which are parallel to one another and with respect to the spindle 50.

Finally, it is seen that the apparatus 30 furthermore includes a handle 58 and, opposite this handle with respect to the mechanical assembly which has just been described, a support 59 on which a vial 60 of lyophilized vaccine is mounted.

As regards operation of the apparatus, reference will now be made to FIGS. 5 to 7.

Figure 1:
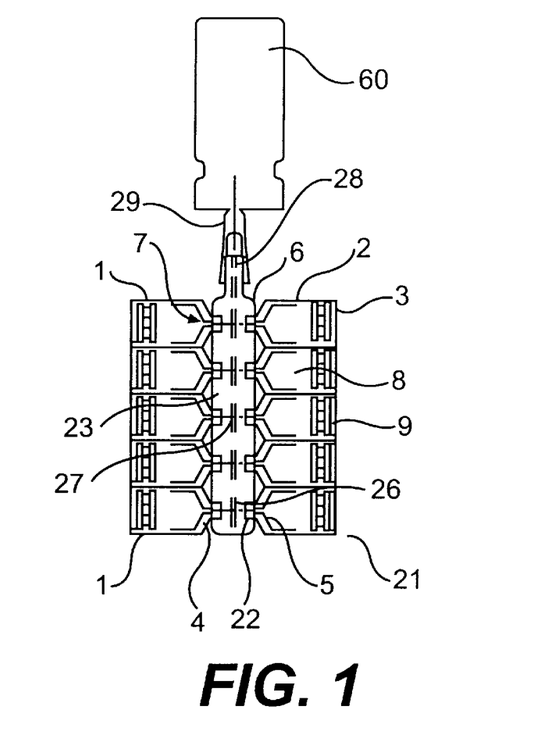
FIG. 1 represents a view in median longitudinal section of an assembly comprising ten carpules on their support piece, of a needle and of a vial of lyophilized vaccine.

FIG. 5 represents the first step, in which an assembly consisting of a cluster 21 of carpules, a needle 29 and a vial 60 (as can be seen in FIG. 1), is placed in the housing 31 of the apparatus 30. At this moment, the operating lever 51 is parallel to the spindles of the jaws, and the double link rods are parallel to one another but are not aligned. The internal jaws are separated from the cluster 21, while being prevented from moving towards one another by the set of shoulders 44 and 45.

In FIG. 6, suitable manipulation of the operating lever 51 causes the external jaws 32 to be displaced, which allows the internal jaws 33 to come to bear against the rear ends of the carpules 1, under the action of the return springs 38. The annular lips 41 are then in part positioned actually inside the carpules 1, if the position of the plunger is initially slightly inserted with respect to the rear end 3 of the carpule, as is seen in the figures.

A cluster of carpules can highly advantageously be positioned by the internal jaws, under the action of their return springs, and by the annular lips penetrating slightly into the carpules.

In FIG. 7, continuing to manipulate the operating lever 51 causes the external jaws 32 to be displaced. As a result of this, the thrust rods 46 slide in the holes 40, and the plungers are pushed until they abut on the end wall 5 of the carpules 1. The studs 48 have penetrated the central recesses 15 of the plungers, and the annular lips 41 are positioned inside the carpules. The solvent contained in the carpules 1 is inside the vial of lyophilized vaccine after having passed through the channels 27 and 26 of the piece 23.

Holding the apparatus by handle 58, the assembly is shaken so as to dissolve the lyophilized vaccine fully. The operating lever 51 is then returned progressively to its initial position in FIG. 5. The engagement of the studs 48 in the central recesses 15 of the plungers 9 causes the latter to be displaced, and the ready-to-use vaccine is thus sucked into the carpules 1. It will be understood that the presence of the annular lips 41 provides a stop effect, making it possible to meter the take-up of liquid and preventing the plungers 9 from becoming aligned with the rear ends 3 of the carpules 1. The annular lips 41 are highly advantageously designed such that the internal volume 8, initially 0.6 ml, is limited by the plunger 9 to 0.5 ml, this being the desired dose, and prevents any air from entering the carpules, given the unavoidable loss of solvent on the walls of the vial in the needle and in the channels.

When the plungers abut against the annular lips, continuing to manipulate the operating lever 51 unhooks the studs 48 and returns to the position in FIG. 5.

It will, of course, be understood that the apparatus 30 thus described could also be used for in situ distribution into carpules of a ready-to-use liquid vaccine contained in a vial, by using a cluster of sterilely packaged empty carpules (carpules which are empty or filled with air or sterile gas). In this case, the support 59 could advantageously be adjustable in order to allow it to receive larger vials from which a plurality of clusters of carpules could be prepared.

Similarly, the invention is not limited to the embodiment described above. The apparatus and the cluster could be intended for a different number of carpules, for example 20. It is also conceivable for a given apparatus to be usable with a cluster having a smaller number of carpules than the clusters for which this apparatus is principally intended. An adjustable support may also be provided in this case. The production of such a support is clearly within the scope of the person skilled in the art and need not therefore be described in detail here. For reasons of bulk, it might, for example, be preferred to use the apparatus described above five times in the case of the 50 dose vials of lyophilized vaccine which are commonly found.

In an improved embodiment, the operating lever is replaced by an electric motor, preferably operating using accumulators. Similarly, the entire jaw actuation mechanism could be produced in different fashion without compromising the principle of the invention.

The invention has been described with reference to carpules, but it will be understood that it is applicable to similar devices, for example single-dose syringes comprising a body, a plunger and a tip for holding an injection needle, and containing a lyophilized preparation, the body and the plunger interacting with the other means of the invention as described for the case of carpules.

Consequently, the term "carpule" will be understood in the present context to mean not only carpules proper but also similar devices.

A preferred embodiment of the invention will now be described.

In contrast to the previous embodiment, provision is made for using a linear arrangement of the carpules.

Figure 8:
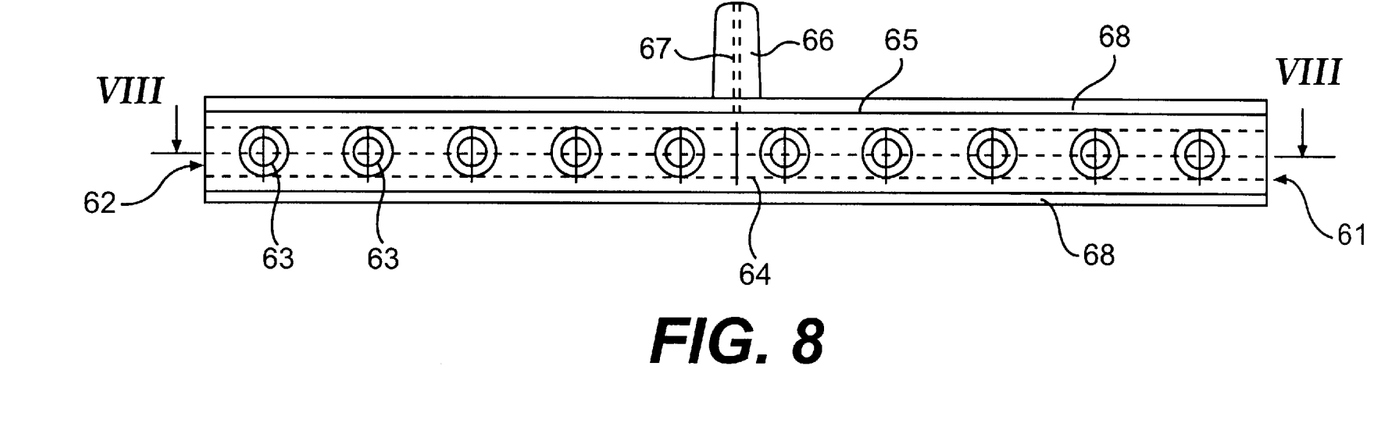
FIG. 8 represents a front view of a support piece according to a second illustrative embodiment.
Figure 9:
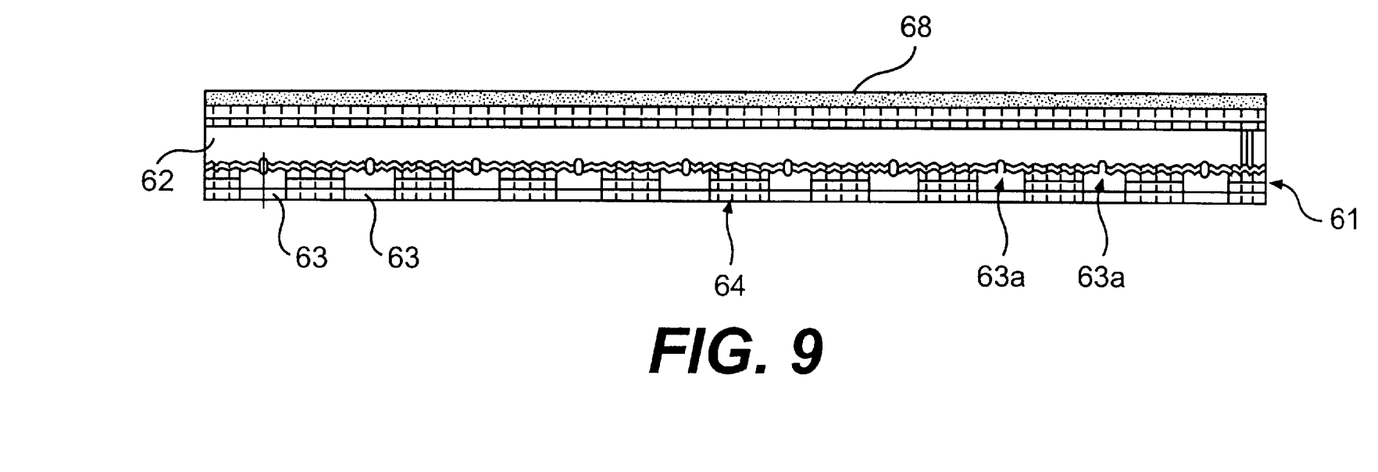
FIG. 9 represents a longitudinal section, on VIII—VIII, of the support piece in FIG. 8.

Instead of the piece 23 in the first illustrative embodiment, use is made of an elongate piece 61 (FIGS. 8 and 9) of square or angular cross-section, including a central channel 62 which opens at both ends and a predetermined number (10 in the embodiment represented) of orifices 63 forming receptacles, which are distributed equidistantly on the same face 64 of the elongate piece 61, these orifices 63 communicating with the central channel 62 via a thin channel 63a and having a profile complementary to that of the head of the carpules, preferably with complementary relief parts for holding the carpules properly in place. It will be noted that these carpules differ from the previous ones merely by their head, which has a relief.

On a face 65 orthogonal to the face 64, the elongate piece 61 includes a projecting part 66 provided with a thin channel 67 connected to the central channel 62. This projecting part forms a tip 66 intended to hold a conventional needle, such as 29 in FIG. 1 (body plus needle proper).

The elongate piece 61, together with its various parts which have just been described, is formed, in particular moulded, integrally from flexible material, such as rubber or another elastic material accepted by the pharmacopoeia, for example from Santoprene.

In order to stiffen this elongate piece 61, a reinforcement 68 is added to it, for example one made of rigid plastic, such as polypropylene, moulded on or attached. The reinforcement 68 represented is a U-shaped section which leaves free the face 64 and a passage for the tip 66.

Figures 10, 11:
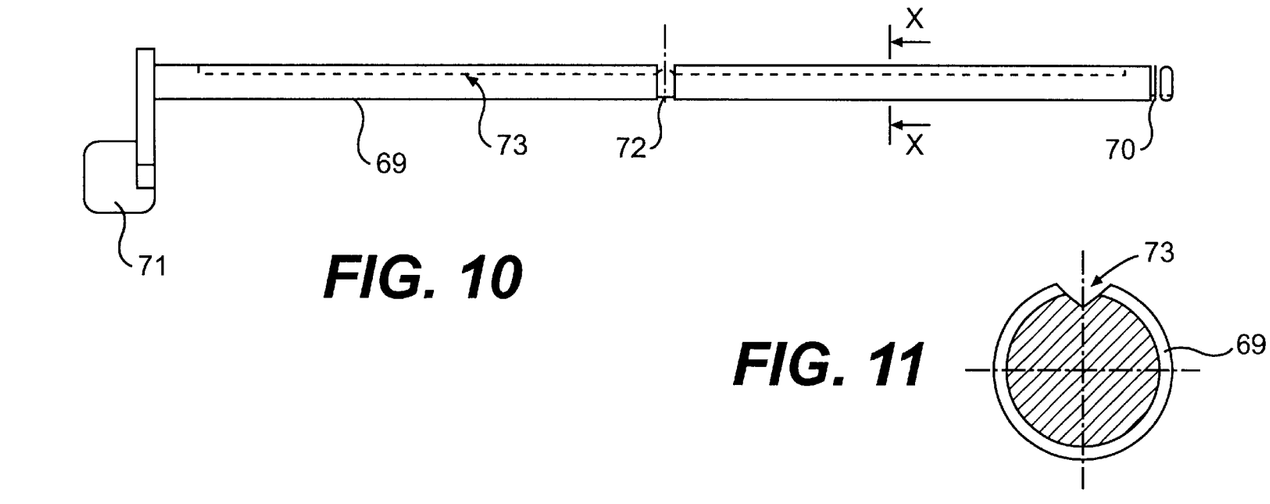
FIG. 10 is a view in elevation of another piece of this second illustrative embodiment, on a larger scale.
FIG. 11 is a view in section, on X—X, of the piece represented in FIG. 1.

The central channel 62, which may, for example, have a diameter of the order of 4 mm, is intended to hold on its inside a rigid spindle 69 (FIG. 10), preferably made of plastic advantageously made of the same material as the carpules and the reinforcement. The spindle 69 is formed by a cylindrical rod which has a slot 70 in the vicinity of one end, a handle 71 at the opposite end, and a central slot or circumferential constriction 72 at the centre. As is seen in section in FIG. 11, and in broken lines in FIGS. 8 and 10, the spindle 69 furthermore includes a groove 73 extending over almost the entire length of the spindle.

Figure 12:
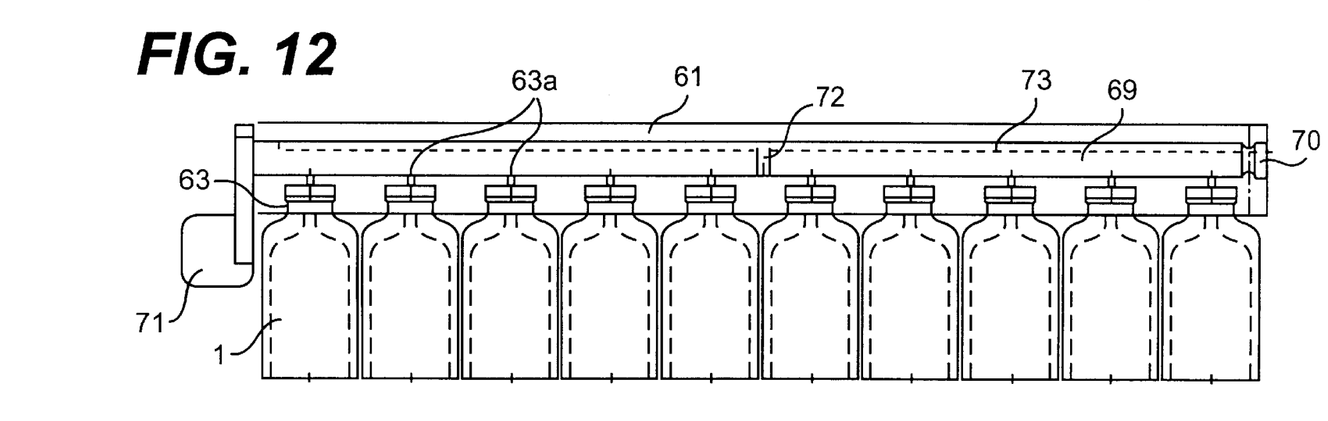
FIG. 12 is a view in elevation of a cluster of carpules according to the second illustrative embodiment.

Reference is now made to FIG. 12, which shows the assembly when put together. The spindle 69 has been fitted into the central channel 62, in which it fits tightly and is held positively by interlocking between the slot 70 and a complementary part moulded integrally with the elongate piece 61. The central slot 72 is axially aligned with the tip 66, so as to communicate with the channel 67 thereof. Carpules 1 are in place, held by their head in the orifices 63 which form receptacles. In the position represented in this figure, the groove 73 lies opposite the orifices 63 and the thin channels 63a, so that the carpules are isolated from one another and from the outside. Only a 180° rotation of the spindle 69 by means of the handle 71 makes it possible to connect all the thin channels 63a with the groove 73 and thereby with the central slot 72 and the channel 67 of the tip 66.

The flexibility of the material constituting the elongate piece 61 makes it possible, in contact with the spindle 69 and the carpules, to make a suitable seal from the outside and between the various orifices and carpules.

Figure 13:
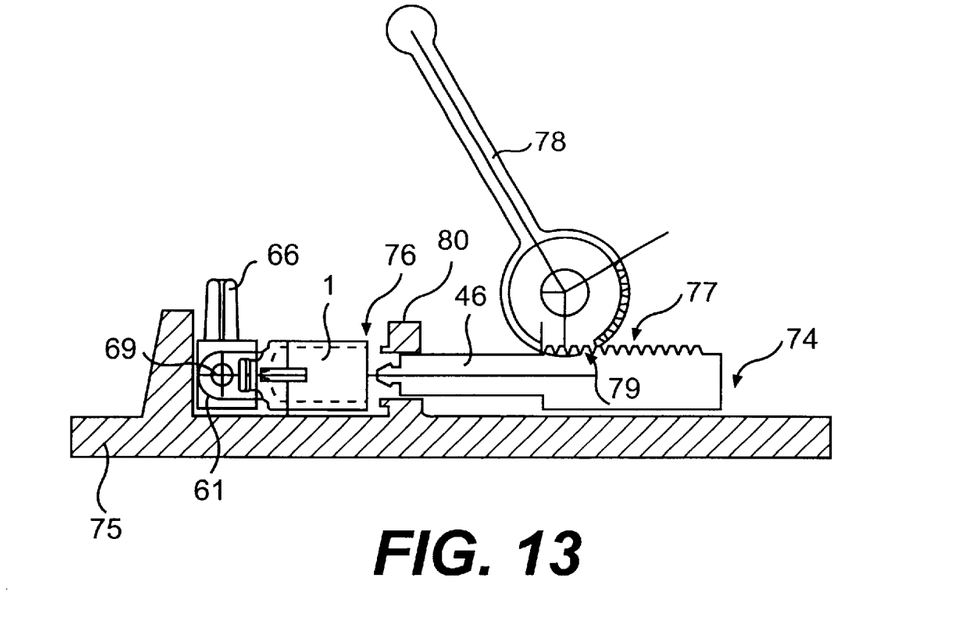
FIGS. 13 and 14 are a schematic view explaining the operation of the second illustrative embodiment.
Figure 14:
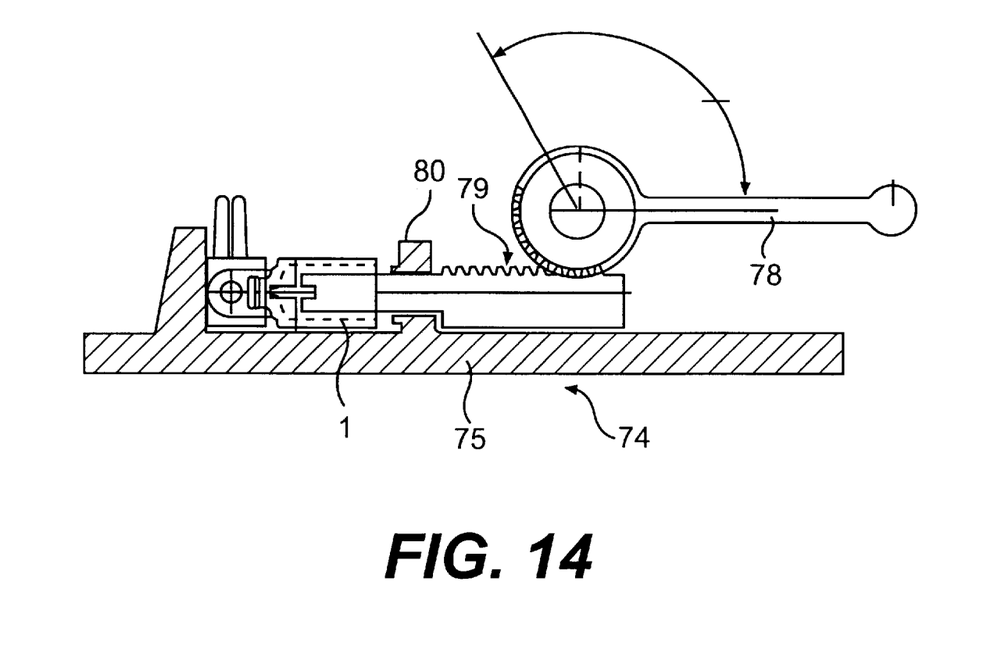

Reference is now made to FIGS. 13 and 14, which schematically represent the distribution apparatus 74, comprising a support plate 75 provided with a housing 76 receiving the assembly which has just been described when put together. The plate is advantageously used by being placed horizontally on a table, with the carpules horizontal and the tip directed vertically and connected, via a needle 29 (not shown) to a vial of product to be dissolved (also not shown).

An actuation means 77 is provided on the support plate 75, this actuation means comprising an operating lever 78 and means 79 for moving in a straight line thrust rods 46 which are essentially similar to those of the previous embodiment, so as to make it possible to actuate the plungers of the carpules 1 in the pressure-application direction and in the suction direction.

Operation is easily understood. After the assembly constituted by the elongate piece 61, the carpules 1 comprising a solvent, the spindle 69, the needle 29 and the vial of product to be dissolved has been put in place, the spindle 69 is turned through 180° in order to connect the carpules 1 and the vial, then the means 79 are actuated so that the thrust rods 46 push on the plungers of the carpules 1 until the solvent contained in the latter passes into the vial. After dissolving, it is merely necessary to actuate the means 79 in the opposite direction in order to suck the ready-to-use preparation into the carpules (it should be noted that the thrust rods 46 and the plungers of the carpules interact as described with reference to the first embodiment). The spindle 69 is then returned to its initial position, so that the filled carpules are isolated from one another and can be used at intervals over time.

The means 79 have not been described in detail. However, the person skilled in the art is entirely capable of designing and producing various solutions for actuating the thrust rods in the manner indicated.

Of course, some particular features described in detail in the first illustrative embodiment can be adopted in the second, in particular the means for adjusting the volume taken into the carpules and the means for releasing the plungers from the thrust rods.

What is claimed is:

1. Assembly for the distribution of a pharmaceutical solution, contained in multi-dose vial, into single-dose carpules for single use, comprising single-dose carpules and a distribution apparatus, in which assembly pressure and suction means are provided, to circulate a liquid from the carpules to the vial and from the vial to the carpules, by means of a network of channels.

2. Assembly according to claim 1, characterized in that it comprises means for controlling the volume of pharmaceutical solution introduced into the carpules.

3. Assembly according to claim 1, wherein the single-dose carpules are formed by a cylindrical body which defines an internal volume in which a plunger slides in leaktight fashion, this plunger being designed to vary the internal volume, the plungers of the single-dose carpules being used as pressure/suction means for circulating the liquid from the carpules to the vial and from the vial to carpules.

4. Assembly according to claim 3, wherein the cylindrical body of the single-dose carpules is closed at one end by a neck having a central orifice forming a nozzle for pressurized-jet injection, the plunger forming said jet.

5. Assembly according to claim 1, wherein the carpules are presented in groups of more than one and are mounted in leaktight fashion and removably on a support piece which has internally a central channel which supplies each of the single-dose carpules of the group via collateral channels, the central channel opening through a part, of the support piece, which is designed so that the central channel can be connected to the internal volume of a multi-dose vial.

6. Assembly according to claim 1, wherein the distribution apparatus includes a housing into which the single-dose carpules are removably fitted, thrust rods, each arranged so that they can engage removably with the plunger of a carpule, and actuation means for displacing the thrust rods and thereby the plungers of the carpules, in the direction tending to reduce the internal volume of these carpules or in the opposite direction, means being provided in order, to release the engagement between the plungers and the thrust rods, when the rods are actuated in said opposite direction, so that each carpule then contains the required volume of pharmaceutical solution.

7. Assembly according to claim 6, wherein the means for releasing the engagement between the plungers and the thrust rods are calibrated annular pieces which are located on the apparatus and the external diameter of which is slightly smaller than the internal diameter of the body of the carpule, the annular pieces being designed to be located inside a carpule body and form a stop for the plunger of the carpule when it is displaced in the direction tending to increase the internal volume of the carpule.

8. Assembly according to claim 5, wherein the support piece has the carpules on one single face.

9. Assembly according to claim 5, wherein the support piece has the carpules on two opposite faces.

10. Assembly according to claim 6, wherein each thrust rod is equipped at one end with an engagement means which is complementary to an engagement means located on the plungers of the carpules.

* * * * *